(12) United States Patent
He et al.

(10) Patent No.: US 8,507,214 B2
(45) Date of Patent: Aug. 13, 2013

(54) ELISA KIT FOR DETECTING LINCOMYCIN

(75) Inventors: Fangyang He, Beijing (CN); Yuping Wan, Beijing (CN); Caiwei Feng, Beijing (CN); Zhengmiao Zhao, Beijing (CN); Caimao Feng, Beijing (CN); Shanliang Wang, Beijing (CN); Xiaoqin Luo, Beijing (CN); Xiaobin Ma, Beijing (CN)

(73) Assignee: Beijing Kwinbon Biotechnology Co., Ltd., Huilongguan Town, Changping District (CN)

( * ) Notice: Subject to any disclaimer, the term of this patent is extended or adjusted under 35 U.S.C. 154(b) by 328 days.

(21) Appl. No.: 12/988,111

(22) PCT Filed: Sep. 27, 2008

(86) PCT No.: PCT/CN2008/001668
§ 371 (c)(1),
(2), (4) Date: Oct. 15, 2010

(87) PCT Pub. No.: WO2009/127094
PCT Pub. Date: Oct. 22, 2009

(65) Prior Publication Data
US 2011/0111440 A1      May 12, 2011

(30) Foreign Application Priority Data

Apr. 16, 2008 (CN) .......................... 2008 1 0104129

(51) Int. Cl.
*G01N 33/535* (2006.01)
*G01N 33/53* (2006.01)
*C12N 5/12* (2006.01)
*C07K 16/44* (2006.01)

(52) U.S. Cl.
USPC ........ 435/7.92; 435/7.93; 435/7.94; 435/345; 422/430; 436/544; 530/388.9; 530/388.1; 530/391.1; 530/391.3; 530/808

(58) Field of Classification Search
None
See application file for complete search history.

(56) References Cited

U.S. PATENT DOCUMENTS 5,998,222 A * 12/1999 Weimer ........................ 436/518
2006/0188523 A1    8/2006 Pei

FOREIGN PATENT DOCUMENTS

| CN | 1766629 | 5/2006 |
| CN | 1811437 | 8/2006 |
| CN | 101256188 | 9/2008 |
| EP | 0 593 1112 A1 * | 4/1994 |

OTHER PUBLICATIONS

Kumar et al. "Enzyme-Linked Immunosorbent Assay for Ultratrace Determination of Antibiotics in Aqueous Samples" J. Environ. Qual. 33:250-256 (2004), pp. 250-256.*
Wu, Je et al., "Screening method for detection of antimicrobial residues in kidney tissue of swine", *Chinese Journal of Animal Quarantine*, (2005), vol. 22, No. 9, pp. 27-29 (w/English abstract).

* cited by examiner

*Primary Examiner* — Christine Foster
(74) *Attorney, Agent, or Firm* — RatnerPrestia

(57) ABSTRACT

The present invention provides an ELISA kit for detecting lincomycin comprising a coating antigen and an enzyme labeled reagent, wherein the coating antigen is selected from the group consisting of a lincomycin hapten-carrier protein conjugate, a lincomycin antibody and a lincomycin anti-antibody; when the coating antigen is the lincomycin hapten-carrier protein conjugate, the enzyme labeled reagent is an enzyme-labeled lincomycin anti-antibody; when the coating antigen is the lincomycin antibody, the enzyme labeled reagent is an enzyme-labeled lincomycin hapten-carrier protein conjugate; and when the coating antigen is the lincomycin anti-antibody, the enzyme labeled reagent is an enzyme-labeled lincomycin hapten-carrier protein conjugate; and the lincomycin hapten is obtained through the condensation reaction between lincomycin and succinic anhydride. The ELISA kit according to the present invention can be used for detecting the content of lincomycin remained in a sample such as an animal tissue (muscle, liver), honey, etc.

5 Claims, 4 Drawing Sheets

Lincomycin—O—X—R

ELISA KIT FOR DETECTING LINCOMYCIN

CROSS-REFERENCE TO RELATED APPLICATIONS

This application is a U.S. National Phase Application of PCT International Application PCT/CN2008/001668, filed Sep. 27, 2008, which claims priority to Chinese Application No 200810104129.1, filed Apr. 16, 2008, the contents of each of which are incorporated herein by reference in their entireties.

TECHNICAL FIELD

The present invention relates to enzyme-linked immunoassay technology. More specifically, the present invention relates to an enzyme-linked immunosorbent assay (ELISA) kit for detecting lincomycin and the use thereof.

BACKGROUND OF THE INVENTION

Figure 1:
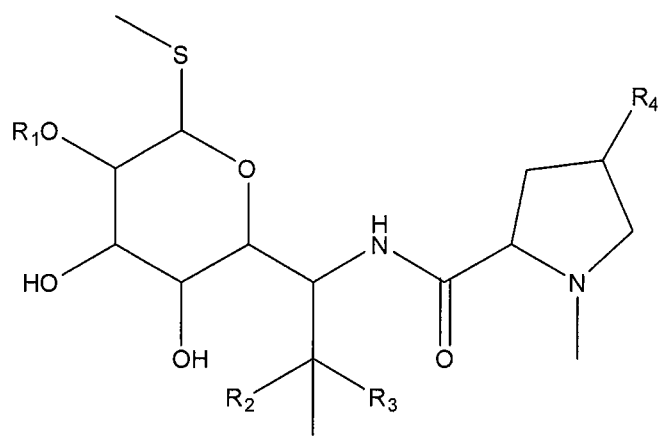

Lincomycin, also known as Jiemycin or LINCOMIX® belongs to lincosamide antibiotics (structural formula as shown in FIG. 1), which is produced by fermentation from Streptomycetaceae (*Streptomyce linoollnensis*), and has strong antibacterial activity. Residual lincomycin enters and accumulates in human body through food chain, leading to drug-resistance of bacteria. Therefore, the content limit of lincomycin is set in many countries. According to Regulation No. 235 of China's Ministry of Agriculture, the residue limit for lincomycin is 0.05 ppm (in eggs). In Japan, it is regulated that the residue limit of lincomycin is 0.02 ppm (in edible chicken bowls).

The conventional methods for detecting the amount of residual lincomycin mainly include high performance liquid chromatography (HPLC), liquid chromatography-tandem mass spectrometry (LC-MS/MS), paper chromatography, etc. Those techniques are not suitable for on-site detection and screen of large numbers of samples due to the equipment, complicated process and high requirement for the manipulative skills of the operators.

SUMMARY OF THE INVENTION

One objective of the present invention is to provide an ELISA kit for detecting lincomycin. The kit of the present invention has advantages of simple operation and less time consuming. The kit of the present invention can be used for rapidly detecting lincomycin in a sample, such as an animal tissue, honey, milk, etc, and is especially suitable for screening a large batch of samples on site.

Another—objective of the present invention is to provide a lincomycin antibody and the preparation method thereof. The lincomycin antibody specifically binds with free lincomycin or lincomycin associated with animal tissues or proteins. The lincomycin antibody is monoclonal antibody or polyclonal antibody.

A further objective of the present invention is to provide a lincomycin hapten and the synthesis method thereof, and a lincomycin immunogen obtained by conjugating the hapten with a carrier protein.

For achieving the above purposes, the present invention provides an ELISA kit for detecting lincomycin comprising a coating antigen and an enzyme labeled reagent, wherein the coating antigen is selected from the group consisting of a lincomycin hapten-carrier protein conjugate, a lincomycin antibody and a lincomycin anti-antibody (secondary antibody); when the coating antigen is the lincomycin hapten-carrier protein conjugate, the enzyme labeled reagent is an enzyme-labeled lincomycin anti-antibody; when the coating antigen is the lincomycin antibody, the enzyme labeled reagent is an enzyme-labeled lincomycin hapten-carrier protein conjugate; and when the coating antigen is the lincomycin anti-antibody, the enzyme labeled reagent is an enzyme-labeled lincomycin hapten-carrier protein conjugate; and the lincomycin hapten is obtained through the condensation reaction between lincomycin and succinic anhydride. The kit may further comprise lincomycin standard solution, color developing solution, concentrated washing solution, stopping solution and concentrated redissolving solution, wherein the concentrated washing solution is 0.1-0.3 mol/L phosphate buffer (pH 7.3-7.9) containing 0.8-1.3 wt % TWEEN® 20 and 0.1-0.6 wt % thiomersal, the concentrated redissolving solution is 0.3-0.7 mol/L phosphate buffer (pH 7.6-8.0); the coating buffer is 0.1-0.3 mol/L boric acid buffer (pH 8.6-9.0); the blocking solution is 0.05 mol/L phosphate buffer (pH 7.2-7.4) containing 8-12 wt % calf serum and 0.03-0.07 wt ‰ sodium azide; the color developing solution consists of developing solution A and developing solution B, wherein said developing solution A is hydrogen peroxide or carbamide peroxide solution, and said developing solution B is o-phenylendiamine or tetramethylbenzidine solution; and said stopping solution is 1-2 mol/L sulfuric acid or hydrochloric acid solution. Preferably, the concentrated washing solution is 0.1 mol/L phosphate buffer (pH 7.3) containing 1.0-1.5 wt % TWEEN® 20 and 0.5 wt % thiomersal as a preservative, the concentrated redissolving solution is 0.2 mol/L phosphate buffer (pH 7.8), the coating buffer is 0.2 mol/L boric acid buffer (pH 9.0); and the blocking solution is 0.05 mol/L phosphate buffer (pH 7.4) containing 8-12 wt % calf serum and 0.03-0.07 wt ‰ sodium azide.

The lincomycin antibody of the present invention is lincomycin monoclonal antibody or lincomycin polyclonal antibody, and is obtained by using the lincomycin hapten-carrier protein conjugate as the immunogen. Said carrier protein may be mouse serum albumin, thyroprotein, bovine serum albumin, rabbit serum albumin, human serum albumin, ovalbumin, hemocyanin or fibrinogen.

The labelling enzyme of the enzyme labeled reagent in the kit of the present invention is horseradish peroxidase or alkaline phosphatase. When the labelling enzyme is horseradish peroxidase, the color developing solution consists of developing solution A and developing solution B, wherein said developing solution A is hydrogen peroxide or carbamide peroxide solution, and said developing solution B is o-phenylendiamine or tetramethylbenzidine solution; and the stopping solution is 1-2 mol/L sulfuric acid or hydrochloric acid solution. When the labelling enzyme is alkaline phosphatase, the color developing solution is nitrophosphate buffer, and the stopping solution is 1-2 mol/L sodium hydroxide solution.

Preferably, the anti-antibody in the kit of the present invention is goat-anti-mouse antibody.

The present invention also provides monoclonal hybridoma cell strain C-1-3 deposited under the accession number CGMCC No. 2398, and the anti-lincomycin monoclonal antibody secreted by the cell strain.

DETAILED DESCRIPTION OF THE INVENTION

Lincomycin, as a small molecule, has immunoreactivity but does not have immunogenicity, and thus can not induce immune response in organisms. For preparing lincomycin-specific antibody, first the structure of lincomycin must be modified so as to obtain a derivative (i.e., lincomycin hapten)

with a structure similar to the parent structure of lincomycin and then the derivative is prepared to have a functional group capable of conjugating with a large molecule of carrier protein so as to obtain lincomycin immunogen or coating antigen via the conjugation.

The lincomycin hapten can be obtained through the reaction between lincomycin and organic small molecules having an active group, such as carboxyl, amino or aldehyde group. The purpose of the reaction is to expose the characteristic group in the parent structure of lincomycin and provide the active group for covalently binding to the large molecule of carrier protein, thereby enhancing the immunogenicity of lincomycin.

Figure 2:
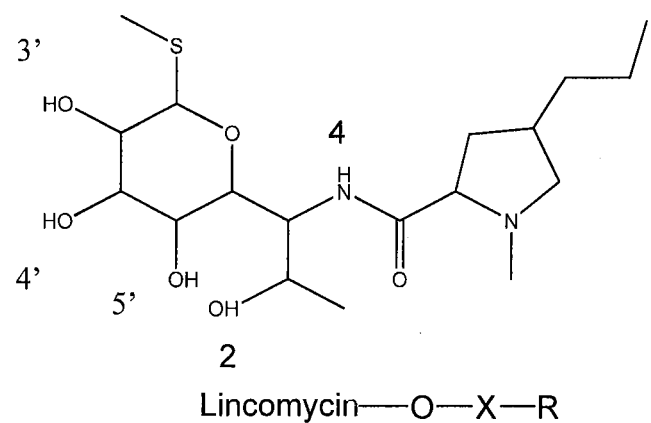

The hapten synthesis process described above is to modify the active group in the structure of lincomycin molecule. Following the differences in the selected groups and binding sites, the specificity and the affinity of the antibody finally obtained are different. The modified sites in the lincomycin molecule and the general structure of the hapten are shown in FIG. 2. In the molecular structure of lincomycin, the positions 3', 4' and 5' in the ring and the position 2 in the branched chain are hydroxyl groups, and the position 4 in the branched chain is imino group. In the structure of lincomycin hapten, X is a small molecular branched chain for exposing the characteristic groups of lincomycin. For example, X may be a branched chain having 3-6 carbon atoms and R is a carboxyl group or an amino group.

Considering the difficulty degree of practical operation, the present invention selects hydroxyl group as the modified site for the hapten, as the hydroxyl group is more active than imino group. As shown in FIG. 2, the hydroxyl groups at positions 3', 4' and 5' are all in the ring, and thus theoretically do not have large difference in their reactive property, the antigen modification and the final preparation of antibodies. The 2-hydroxyl group in the branched chain is significantly different from the above three hydroxyl groups. Therefore, the present invention uses two technical solutions, i.e., modifying the hydroxyl group in the ring of lincomycin and the hydroxyl group in the branched chain of lincomycin, respectively, and selects a preferred solution according to the difference between the antibodies finally prepared.

Figure 3:
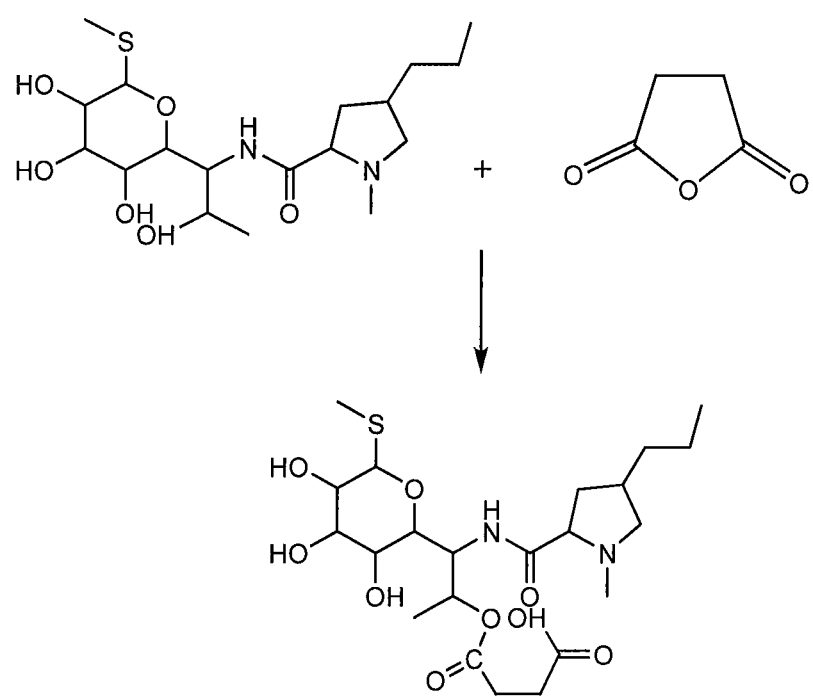
Figure 4:
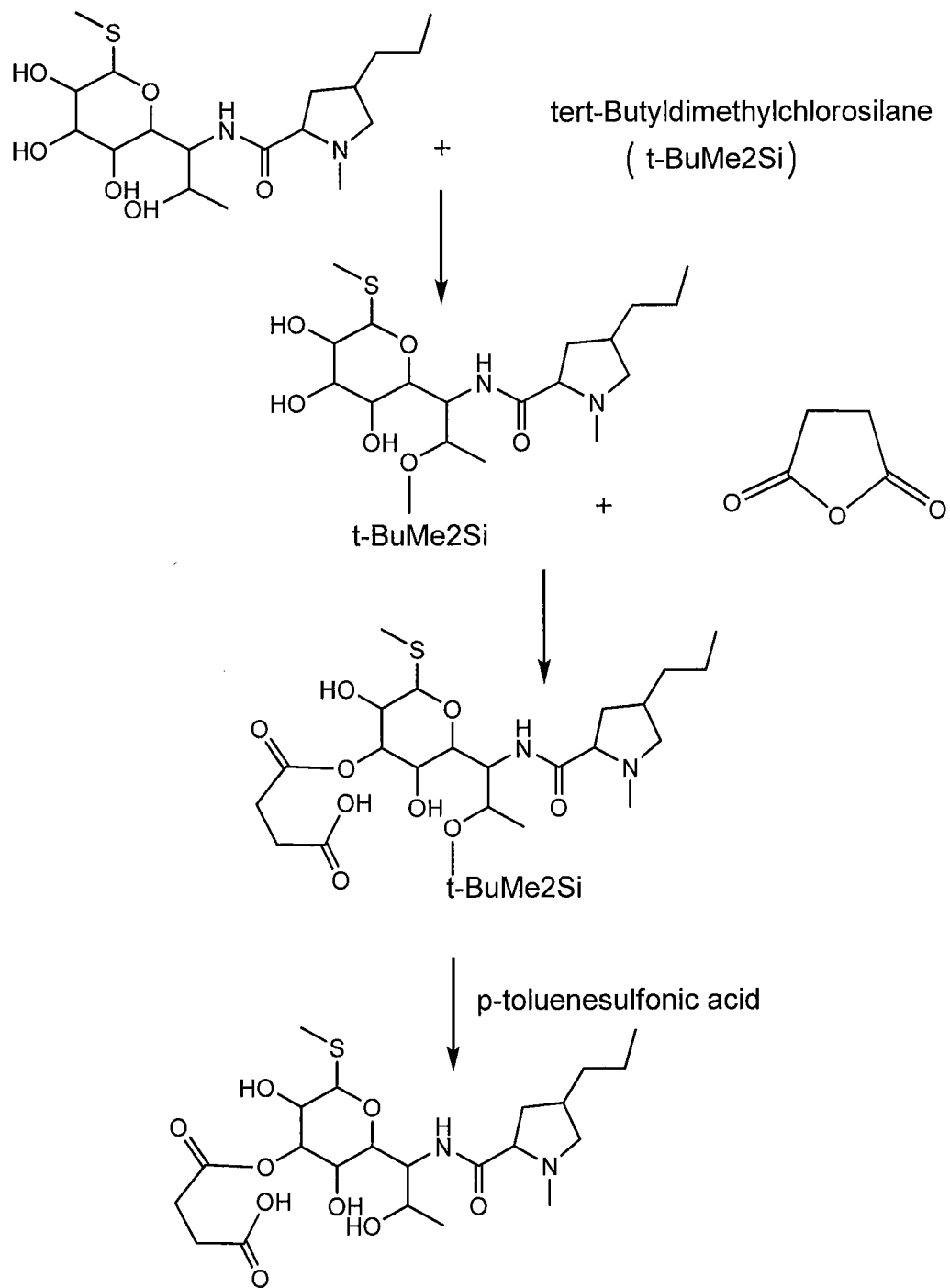

Two lincomycin-hemisuccinate haptens are shown in FIGS. 3 and 4, respectively. In FIG. 3, lincomycin reacts with succinic anhydride directly. Due to the difference of the steric hindrances of the hydroxyl groups, succinic anhydride binds with 2-hydroxyl group in the branched chain so as to obtain hapten LIN-S1. In FIG. 4, succinic anhydride binds with the hydroxyl group in the ring due to the presence of a protecting group, and hapten LIN-S2 is finally obtained through the hydrolysis reaction of the branched chain. The differences between the effects of the antibodies prepared from the above two haptens are described in detail in the following part of the present invention.

The carrier protein for binding with the above hapten may be a conventional carrier protein, such as one selected from mouse serum albumin, thyroprotein, bovine serum albumin, rabbit serum albumin, human serum albumin, ovalbumin, hemocyanin and fibrinogen. Those proteins are rich in the functional groups capable of covalently binding with lincomycin hapten, such as carboxyl group, amino group, etc.

According to the present invention, lincomycin hapten is conjugated with the carrier protein using mixed anhydride method or carbodiimide method, so as to expose the characteristic group of lincomycin, and enhance the immunogenicity of lincomycin. In the present invention, the molar ratio of lincomycin to the carrier protein, such as bovine serum albumin, is preferably 12~15:1 as determined by the experiments.

The lincomycin-specific antibody of the present invention may be lincomycin monoclonal antibody or lincomycin polyclonal antibody. Preferably, the lincomycin monoclonal antibody is lincomycin-specific mouse monoclonal antibody, more preferably the monoclonal antibody secreted by hybridoma cell strain C-1-3 (CGMCC No. 2398).

The hybridoma cell strain C-1-3 (CGMCC No. 2398) (classification and nomenclature: monoclonal hybridoma cell strain against lincomycin) secreting the lincomycin monoclonal antibody has been deposited in China General Microbiological Culture Collection Center (Abbr.: CGMCC; address: Institute of Microbiology, Chinese Academy of Sciences, Datun Road, Chaoyang District, 100101) on Mar. 12, 2008.

The lincomycin polyclonal antibody may be antibodies derived from mouse, horse, goat, rabbit or guinea pig, among which rabbit polyclonal lincomycin antibody is preferred.

The main technical content of the present invention is described in details as follows.

The experimental methods described in the present invention can be carried out by a skilled person with reference to "Technology of Enzyme Immunoassay", Liguo Yang, Shaochang Hu, Pinghua Wei, et al., Nanjing University Press, 1998.

1. Synthesis of Hapten

Because of the different steric hindrances of the four hydroxyl groups, hapten LIN-S1 is obtained from lincomycin through the succinic anhydride method. The synthetic scheme is shown in FIG. 3.

As 2-hydroxyl group has the smallest steric hindrance, hapten LIN-S2 can be obtained by selectively protecting 2-hydroxyl group with t-butyl-dimethyl chlorosilane, then acylating 4'-hydroxyl group in the ring through succinic anhydride method, and removing the protective group via hydrolysis in the presence of p-toluenesulfonic acid. The synthetic scheme is shown in FIG. 4.

2. Preparation of Lincomycin Antibody (1) Preparation of Immunogen

The immunogen is obtained by conjugating the lincomycin hapten with a carrier protein through mixed anhydride method.

(2) Preparation of Lincomycin Mouse Monoclonal Antibody a) Immunization procedure of animals: Baclb/c mice are used as the animal for immunization and the lincomycin hapten-carrier protein conjugate is used as the immunogen. When the serum titer is higher than 1:3000, the spleen is taken for cell fusion.

b) Cell fusion and cloning: The spleen cells from immunized Baclb/c mouse are fused with SP2/0 myeloma cells, and a hybridoma cell strain stably expressing monoclonal antibody is obtained through screening.

c) Identification of preferred monoclonal antibody: The properties of the monoclonal antibodies prepared from the above two schemes are detected. The specificity and sensitivity of the antibody prepared from LIN-S1 are higher than those of the antibody prepared from LIN-S2.

(3) Preparation of Lincomycin Rabbit Polyclonal Antibody

A New Zealand rabbit is selected as the animal for immunization and the lincomycin hapten-carrier protein conjugate is used as the immunogen. The antibody titer in serum is detected after several immunizations. When the titer is higher than 1:10000, the rabbit is euthanized, and the serum is collected to obtain the polyclonal antibody.

3. Preparation of Anti-Antibody (1) goat-anti-mouse antibody: the goat-anti-mouse antibody is obtained from a pathogen-free goat immunized by immunizing the goat with the mouse antibody as the immunogen.

(2) goat-anti-rabbit antibody: the goat-anti-rabbit antibody is obtained from a pathogen-free goat immunized by immunizing the goat with the rabbit antibody as the immunogen.

4. The Method for Detecting Lincomycin and the Detection Kit According to the Present Invention can be Used for Detecting Lincomycin in the Samples, Such as Animal Tissues, Honey, Etc.

The kit of the present invention comprises a coating antigen and an enzyme labeled reagent. The kit may further comprise lincomycin standard solutions, color developing solution, stopping solution, concentrated washing solution, and concentrated redissolving solution.

The coating antigen is a lincomycin hapten-carrier protein conjugate, a lincomycin antibody or a lincomycin anti-antibody. The enzyme labeled reagent is an enzyme-labeled antibody, an enzyme-labeled lincomycin hapten-carrier protein conjugate (the lincomycin hapten-carrier protein conjugate is also referred to as lincomycin-conjugated antigen herein) or an enzyme-labeled lincomycin anti-antibody. When the coating antigen is the lincomycin hapten-carrier protein conjugate, the enzyme labeled reagent is an enzyme-labeled lincomycin anti-antibody; when the coating antigen is the lincomycin antibody, the enzyme labeled reagent is an enzyme-labeled lincomycin-conjugated antigen; and when the coating antigen is the anti-antibody, the enzyme labeled reagent is an enzyme-labeled lincomycin-conjugated antigen.

The lincomycin standard solutions can be solutions at concentrations of 0 μg/L, 0.2 μg/L, 0.6 μg/L, 1.8 μg/L, 5.4 μg/L and 16.2 μg/L, respectively.

The labelling enzyme of the enzyme labeled reagent is horseradish peroxidase or alkaline phosphatase, wherein horseradish peroxidase is preferred. The enzyme-labeled goat-anti-mouse antibody or goat-anti-rabbit antibody is obtained by conjugating the labelling enzyme with the anti-antibody through glutaraldehyde method or sodium periodate method.

When the labelling enzyme is horseradish peroxidase, the color developing solution consists of developing solution A and developing solution B, wherein said developing solution A is hydrogen peroxide or carbamide peroxide solution and said developing solution B is o-phenylendiamine or tetramethylbenzidine solution, and the stopping solution is 1-2 mol/L sulfuric acid or hydrochloric acid solution. When the labelling enzyme is alkaline phosphatase, the developing solution is p-nitrophosphate buffer, and the stopping solution is 1-2 mol/L sodium hydroxide solution.

The concentrated washing solution may be 0.1-0.3 mol/L phosphate buffer (pH 7.3-7.9) containing 0.8-1.3 wt % TWEEN® 20 and 0.1-0.6 wt % thiomersal. The concentrated redissolving solution is 0.3-0.7 mol/L phosphate buffer (pH 7.6-8.0).

5. Detection Principle of the Present Invention

When the ELISA plate is precoated with lincomycin-conjugated antigen, the solution of lincomycin-specific antibody is added after adding the sample solution or standard solution. The residual lincomycin in the sample competes with the lincomycin-conjugated antigen coated on the ELISA plate for the lincomycin-specific antibody. The enzyme-labeled lincomycin anti-antibody is added for amplifying the effects. The developing solution is added for developing the color. The absorbance of the sample is negatively correlated with the content of lincomycin. The content of the residual lincomycin can be calculated by comparing with the standard curve. Meanwhile, by comparing the color of the ELISA plate with the colors of the lincomycin standard solutions at series of concentrations, the concentration range of the residual lincomycin in the sample can be roughly determined.

When the ELISA plate is precoated with the lincomycin-specific antibody, the solution of the enzyme-labeled lincomycin-conjugated antigen is added after adding the sample solution or standard solution. The residual lincomycin in the sample competes with the enzyme-labeled antigen for the lincomycin-specific antibody coated on the ELISA plate. The developing solution is added for developing the color. The absorbance of the sample is negatively correlated with the content of lincomycin. The content of the residual lincomycin can be calculated by comparing with the standard curve. Meanwhile, by comparing the color of the ELISA plate with the colors of the lincomycin standard solutions at a series of concentrations, the concentration range of the residual lincomycin in the sample can be roughly determined.

When the ELISA plate is precoated with lincomycin-conjugated antigen, the solution of lincomycin-specific antibody is added after adding the sample solution or standard solution. The residual lincomycin in the sample competes with the lincomycin-conjugated antigen coated on the ELISA plate for the lincomycin-specific antibody. The developing solution is added for developing the color. The absorbance of the sample is negatively correlated with the content of lincomycin. The content of the residual lincomycin can be calculated by comparing with the standard curve. Meanwhile, by comparing the color of the ELISA plate with the colors of the lincomycin standard solutions at a series of concentrations, the concentration range of the residual lincomycin in the sample can be roughly determined.

When the ELISA plate is precoated with anti-antibody, the lincomycin-specific antibody is added and incubated for a period, and a solution of lincomycin-conjugated antigen is added after adding a sample solution or standard solution. The residual lincomycin in the sample competes with the lincomycin-conjugated antigen for the lincomycin-specific antibody. The developing solution is added for developing the color. The absorbance of the sample is negatively correlated with the content of lincomycin. The content of the residual lincomycin can be calculated by comparing with the standard curve. Meanwhile, by comparing the color of the ELISA plate with the colors of the lincomycin standard solutions at a series of concentrations, the concentration range of the residual lincomycin in the sample can be roughly determined.

6. The Present Invention Also Provides a Method for Detecting Lincomycin, Comprising the Steps of:
1) pre-treating the samples;
2) detecting with the kit above; and
3) analyzing the detection result.

The pretreatment step of the sample is mainly for obtaining lincomycin solution from the sample and used for the subsequent detections.

According to the present invention, when the kit is used, the specific protocols are as follows:

When the coating antigen is a lincomycin-conjugated antigen, the standard solution or sample solution is added into the microtiter wells of the ELISA plate, and then the antibody is added. After incubating, the plates are washed, the liquid in the microtiter wells is removed, and the residual liquid is absorbed with absorbent paper. The enzyme-labeled lincomycin anti-antibody is then added. After incubating, the plates are washed, the liquid in the microtiter wells is removed, and the residual liquid is absorbed with absorbent paper. The reaction is stopped after the color development. The absorbance is detected with Micro-plate Reader;

When the coating antigen is a lincomycin-conjugated antigen, the standard solution or sample solution is added into the microtiter wells of the ELISA plate, and then the enzyme-labeled antibody is added. After incubating, the plates are washed, the liquid in the microtiter wells is removed, and the residual liquid is absorbed with absorbent paper. The reaction is stopped after the color development. The absorbance is detected with Microplate Reader;

When the coating antigen is lincomycin-specific antibody, the standard solution or sample solution is added into the microtiter wells of the ELISA plate, and then the enzyme-labeled lincomycin hapten is added. After incubating, the plates are washed, the liquid in the microtiter wells is removed, and the residual liquid is absorbed with absorbent paper. The reaction is stopped after the color development. The absorbance is detected with Microplate Reader;

When the coating antigen is the anti-antibody, the lincomycin-specific antibody is added into the microtiter wells of the ELISA plate. After incubating, the plates are washed, the liquid in the microtiter wells is removed, and the residual liquid is absorbed with absorbent paper. The standard solution or sample solution is added, and then the enzyme-labeled lincomycin hapten is added. After incubating, the plates are washed, the liquid in the microtiter wells is removed, and the residual liquid is absorbed with absorbent paper. The reaction is stopped after the color development. The absorbance is detected with Microplate Reader.

The detection result is analyzed by dividing the average absorbance (B) of the standard solution of each concentration with the absorbance ($B_0$) of the first standard solution (blank standard) and multiplying by 100% to obtain the percent absorbance.

The calculation formula is shown as:

Percent absorbance (%)=$(B/B_0)\times 100\%$.

A standard curve is plotted with the semi-log value of the concentrations (μg/L) of the lincomycin standard solutions as X axis, and the percent absorbance as Y axis. The percent absorbances of the sample solutions are calculated according to the same method. The concentration corresponding to each sample can be obtained from the standard curve.

The detection result can also be analyzed by calculating the concentration of the sample solution with regression equation.

THE BRIEF DESCRIPTION OF THE DRAWINGS

Figure 5:
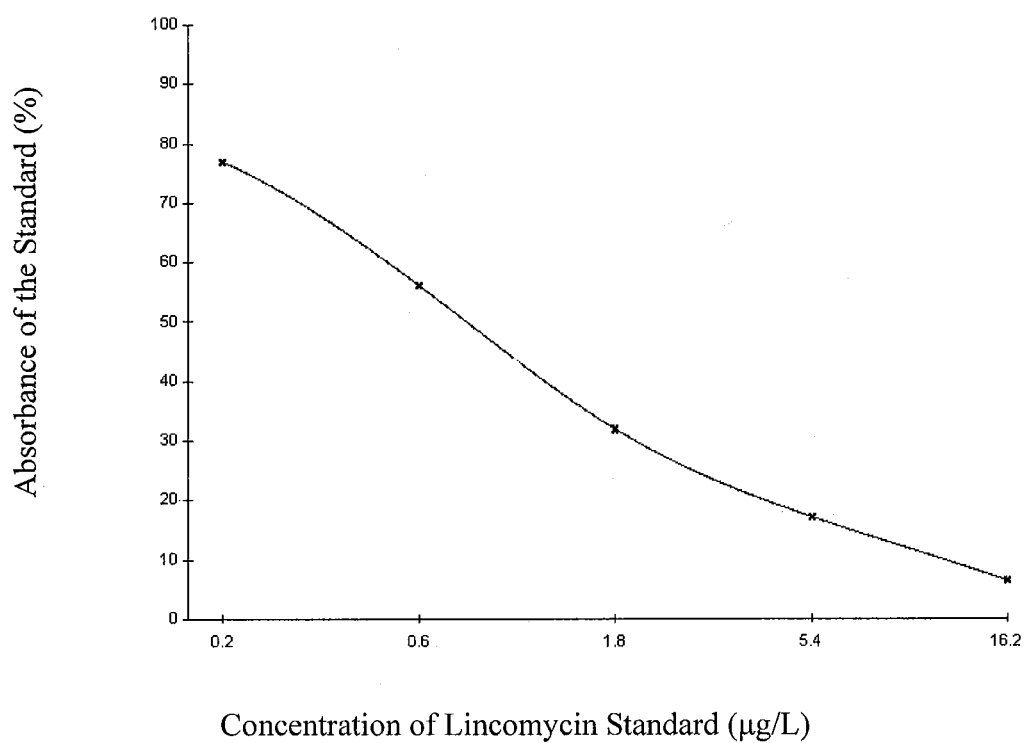

FIG. 1: General chemical formula of lincosamide antibiotics wherein R1=H; R2=OH; R3=H; R4=$C_3H_7$;
FIG. 2: Modified Structural sites for lincomycin hapten;
FIG. 3: Synthetic scheme of lincomycin hapten LIN-S1;
FIG. 4: Synthetic scheme of lincomycin hapten LIN-S2; and
FIG. 5: Standard curve of the kit.

SPECIFIC MODE OF CARRYING OUT THE INVENTION

The present invention will be further described with reference to the specific examples below. It should be appreciated that those examples are only used for illustrating the present invention, but not for limiting the scope thereof.

Example 1

Preparation of the Components of the Kit

1. Synthesis of Antigen
  a. Synthesis of Hapten
  Lincomycin hapten having carboxyl group is prepared according to succinic anhydride method.
  Hapten LIN-S1 is obtained by the steps of: weighting 2.3 g lincomycin hydrochloride (purchased from Dr Com, Germany, Cat no. C14635000) and 0.5 g succinic anhydride, placing into a 50 ml round flask, adding anhydrous pyridine till the lincomycin hydrochloride and succinic anhydride are completely dissolved, and reacting at 70° C. for 24 h under stirring; removing the solvent via distillation under reduced pressure after the reaction is finished, washing the residues with acetone for several times and then with 2-3 times volume of ethyl acetate/n-hexane (2:1, v/v), adequately vibrating, and crystallizing to obtain the lincomycin hemisuccinate hapten.

The hapten LIN-S2 is obtained by the steps of:
Weighting 1.59 g lincomycin, placing into a 25 ml round flask, adding 6 ml N,N-dimethyl formamide (DMF) to dissolve the lincomycin, successively adding 1.41 g imidazole and 1.56 g t-butyl dimethylchlorosilane (t-BuMe$_2$Si—Cl) under stirring, further stirring at 30° C. for 2 h, extracting the product with ethyl acetate, concentrating the extract with a rotary evaporator, and then drying in vacuum for 24 h to obtain 4-O-t-BuMe$_2$Si-LIN.

Placing 0.56 g 4-O-t-BuMe$_2$Si-LIN and 0.1 g succinic anhydride into a 50 ml round flask, adding anhydrous pyridine till 4-O-t-BuMe$_2$Si-LIN and succinic anhydride are completely dissolved, and reacting at 70° C. under stirring for 24 h, removing the solvent via distillation under reduced pressure after the reaction is finished, washing the residues with acetone for several times, washing the residues with ethyl acetate which is 2-3 times volume of the residues, vibrating adequately, concentrating the ethyl acetate extract with a rotary evaporator, and drying in vacuum for 24 h to obtain 4-O-t-BuMe$_2$Si-2-O-lincomycin hemisuccinate;

Placing 0.3 g 4-O-t-BuMe$_2$Si-2-O-lincomycin hemisuccinate into a 50 ml round flask, adding 17 mL methanol for dissolving 4-O-t-BuMe$_2$Si-2-O-lincomycin hemisuccinate, adding dropwise 0.26 g p-toluenesulfonic acid hydrate in 10 ml methanol solution, continuously stirring for 25 min, removing methanol via rotary evaporation, after partitioning of the product between the aqueous layer and the ethyl acetate layer, concentrating the ethyl acetate layer with a rotary evaporator, and then drying in vacuum for 24 h to obtain hapten LIN-S2.

b. Synthesis of Immunogen
By the way of illustration, as described below, an immunogen is obtained from lincomycin hapten and bovine serum albumin through mixed anhydride method.

The procedure specifically comprises the following steps:
Dissolving 5.8 mg lincomycin hapten into 0.1 ml N,N'-dimethyl formamide (DMF), cooling to 10° C., adding 2 μl isobutyl chloroformate, reacting at 10° C. for 30 min under stirring; dissolving 60 mg bovine serum albumin in 2 ml 50 mmol/L Na$_2$CO$_3$, reacting at 10° C. for 4 h, staying at 4° C. overnight, loading onto a SEPHADEX® G-25 column, equilibrium and eluting with a buffer solution (0.2 mol/L phosphate buffer, pH 7.4), pooling the fractions containing bovine serum albumin, placing the pooled fractions into a dialysis tubing, and dialyzing in 0.2 mol/L phosphate buffer (pH 7.4) for 7 days while changing the dialysis buffer 3-4 times per day. The immunogen thus obtained is freeze-dried for storage. Through detection, the binding molar ratio of lincomycin hapten to the carrier protein is 13:1.

c. Preparation of the Coating Antigen of Lincomycin-Conjugated Antigen
By the way of illustration, as described below, a coating antigen is obtained by conjugating lincomycin hapten with ovalbumin.

The procedure specifically comprises the following steps:
Dissolving 5.8 mg lincomycin hapten in 0.1 ml DMF, cooling to 10° C., adding 2 μl isobutyl chloroformate, reacting at 10° C. for 30 min under stirring; dissolving 30 mg ovalbumin in 2 ml 50 mmol/L $Na_2CO_3$, reacting at 10° C. for 4 h, staying at 4° C. overnight, loading onto a SEPHADEX® G-25 column, balancing and eluting with a buffer solution (0.2 mol/L phosphate buffer, pH 7.4), pooling the fractions containing ovalbumin, placing the pooled the fractions into a dialysis tubing, and dialyzing in 0.2 mol/L phosphate buffer (pH 7.4) for 7 days while changing the dialysis buffer 3-4 times per day. The immunogen thus obtained is freeze-dried for storage. Through detection, the binding molar ratio of lincomycin hapten to the carrier protein is 15:1.

2. Preparation of Monoclonal Antibody a. Immunization of Animals

Healthy Balb/c mice 6-8 weeks old are selected and immunized at a dosage of 100 μg per one mice. For the first immunization, the immunogen is well mixed with complete Freund's adjuvant (purchased from Sigma Inc., -Cat no. F5881) at equal amount. For the follow-up immunization, the immunogen is mixed with incomplete Freund's adjuvant (purchased from Sigma Inc., Cat no. F5506).

b. Cell Fusion and Cloning

When the mouse serum titer is determined as high, the spleen cells are collected and fused with SP2/0 myeloma cells at an amount ratio of 7:1. The cell supernatant is detected by indirect competitive ELISA for screening the positive wells. The cells in the positive wells are cloned via limiting dilution method until a hybridoma cell secreting monoclonal antibody is obtained.

c. Identification of the Preferred Cell Strains of Monoclonal Antibody

The 50% inhibitory concentration and specificity of the monoclonal antibodies prepared from the two hapten schemes above are detected. The results are shown in the table below.

TABLE 1

Detecting results of the properties of the antibodies obtained from the two hapten schemes

| | | Technical schemes | |
| --- | --- | --- | --- |
| Technical indexes | | LIN-S1 | LIN-S2 |
| $IC_{50}$ | | 0.4 μg/kg | 489 μg/kg |
| Cross reaction | Lincomycin | 100% | 100% |
| | Clindamycin | <1% | 13.1% |
| | Erythromycin | <1% | <1% |
| | Tylosin | <1% | <1% |
| | Streptomycin | <1% | 9.2% |
| | Kanamycin | <1% | 14.7% |

As shown in Table 1, the antibody prepared from hapten LIN-S2 exhibits cross reaction with several antibiotics, has low specificity with $IC_{50}$ of 489 μg/kg, and can not satisfy the requirement for detection of residual lincomycin.

Therefore, according to the present invention, lincomycin monoclonal antibody prepared from hapten LIN-S1 is selected as the preferred antibody. This antibody is secreted by hybridoma cell strain C-1-3 (CGMCC No. 2398), and has high specificity to lincomycin with $IC_{50}$ of 0.4 μg/kg.

d. Freezing and Thawing of the Cells

The monoclonal hybridoma cell strain against lincomycin may be prepared into suspensions with cryopreservation solution at $1 \times 10^6$ cells/ml, and stored in liquid nitrogen for a long term. When the cells are to be recovered, the cryopreservation tube is taken out from liquid nitrogen, and immediately placed into a water bath at 37° C. for thawing. The cryopreservation solution is removed via centrifuge, and the cells are removed into a flask for culture.

e. Production and Purification of the Monoclonal Antibody

Sterile paraffin oil is injected intraperitoneally into several Balb/c mice 6-8 weeks old at 0.5 mg/one mice. The monoclonal hybridoma cell strain against lincomycin is intraperitoneally injected at $0.5 \times 10^7$ cells/one mice after 7 days. The ascites are collected after another 7 days, purified according to caprylic acid-saturated ammonium sulfate method, and stored at −20° C.

2. Preparation of Polyclonal Antibody

New Zealand rabbit is selected as the animal for immunization, and immunized with the conjugate of lincomycin hapten and bovine serum albumin as the immunogen at a dosage of 1.5 mg/kg. For the first immunization, the immunogen is mixed with complete Freund's adjuvant (for the source, see ibid) at equal amount to obtain an emulsion, and subcutaneously injected into neck and back at multiple sites. After an interval of 3-4 weeks, the immunogen is mixed with incomplete Freund's adjuvant (for the source, see ibid) at equal amount to obtain emulsion and then used for booster immunization. The animals receive 5 immunizations in total. For the last immunization, no adjuvant is added. Ten days after the last immunization, the antibody titer in the serum is detected. The blood is collected from heart, and the polyclonal antibody is obtained by purification according to caprylic acid-saturated ammonium sulfate method.

3. The goat-anti-mouse antibody is prepared by the steps of: using goat as the animal to be immunized, and immunizing pathogen-free goat with the immunogen of mouse antibody. The goat-anti-rabbit antibody is prepared by the steps of: using goat as the animal to be immunized, and immunizing pathogen-free goat with the immunogen of rabbit antibody.

4. Preparation of the ELISA Plate a. Preparation of Solutions

Coating buffer: 0.2 mol/L boric acid buffer, pH 8.6. The coating buffer is prepared by weighting 10.49 g $Na_2B_4O_7 \cdot 10H_2O$ and 5.57 g $H_3BO_3$, and dissolving in 1 L deionized water.

Blocking solution: 0.05 mol/L phosphate buffer (pH 7.2) containing 10 wt % calf serum and 0.05 wt ‰ sodium azide. The blocking solution is prepared by weighting 12.90 g $Na_2HPO_4 \cdot 12H_2O$, 2.18 g $NaH_2PO_4 \cdot 2H_2O$ and 5 g sodium azide, dissolving in deionized water, adding 100 mL calf serum, and fixing the volume to 1 L.

Concentrated washing solution: 0.2 mol/L phosphate buffer (pH 7.4) containing 1.0 wt % TWEEN® 20 and 0.5 wt % thiomersal. The concentrated washing solution is prepared by weighting 14.51 g $Na_2HPO_4 \cdot 12H_2O$, and 1.48 g $NaH_2PO_4 \cdot 2H_2O$, dissolving in deionized water, adding 10 mL TWEEN® 20 and 5 g thiomersal, and fixing the volume to 1 L with deionized water.

Diluted washing solution: an appropriate amount of the concentrated washing solution is mixed with deionized water at a volume ratio of 1:19 for further use.

Concentrated redissolving solution: 0.2 mol/L phosphate buffer (pH 7.4) containing 5% bovine serum albumin. The concentrated redissolving solution is prepared by weighting 14.51 g $Na_2HPO_4 \cdot 12H_2O$, and 1.48 g $NaH_2PO_4 \cdot 2H_2O$, dissolving in deionized water, adding 50 g bovine serum albumin, and fixing the volume to 1 L with deionized water.

b. Coating of the ELISA Plate

Diluting the lincomycin-conjugated antigen, lincomycin antibody or lincomycin anti-antibody with the coating buffer to 0.05-2 μg/ml, adding into the microtiter wells at 100 μl/well, incubating at 37° C. for 2 hours or at 4° C. overnight, removing the coating buffer, washing with the 20-time-diluted concentrated washing solution twice for 30 seconds each time, removing the liquid in the wells, and absorbing the residual liquid with absorbent paper, adding 200 ml blocking solution into each well, incubating at 37° C. for 2 hours, removing the liquid in the wells, drying and then sealing the wells with Al film, and storing at 4° C. in dry places for further use.

5. Enzyme-Labeled Goat-Anti-Mouse Anti-Antibody

The horseradish peroxidase-labeled goat-anti-mouse anti-antibody of the present invention is obtained by conjugating the labeling enzyme with the anti-antibody according to the glutaraldehyde method or sodium periodate method.

Example 2

Construction of ELISA Kit for Detecting Lincomycin

The ELISA kit for detecting lincomycin is constructed to comprise the following components:
(1) an ELISA plate coated with lincomycin-conjugated antigen;
(2) horseradish peroxidase-labeled goat-anti-mouse anti-antibody;
(3) working solution of lincomycin monoclonal antibody;
(4) 6 vials of lincomycin standard solution at concentrations of 0 μg/L, 0.2 μg/L, 0.6 μg/L, 1.8 μg/L, 5.4 μg/L and 16.2 μg/L, respectively;
(5) color developing solution consisting of developing solution A and developing solution B, wherein the developing solution A is carbamide peroxide solution, and the developing solution B is tetramethylbenzidine solution;
(6) stopping solution: 2 mol/L hydrochloric acid;
(7) concentrated washing solution: 0.2 mol/L phosphate buffer (pH 7.4) containing 1.0 wt % TWEEN® 20 and 0.5 wt % thiomersal; and
(8) concentrated redissolving solution: 0.2 mol/L phosphate buffer (pH 7.4) containing 5% bovine serum albumin.

Example 3

Detection of Lincomycin in Real Samples

1. Pre-Treatment of the Samples
   a) Preparation of the Solutions
   0.015 mol/L hydrochloric acid solution (special use for animal tissue samples) is prepared by adding 1.25 ml concentrated hydrochloric acid solution into a container containing deionized water, and fixing the volume to 1 L.
   Methanol-hydrochloric acid solution (special for animal tissue samples) is prepared by uniformly mixing 10 ml methanol and 60 ml 0.015 mol/L hydrochloric acid solution.
   Redissolving solution is prepared by diluting the concentrated redissolving solution with deionized water at a volume ratio of 1:1 and mixing for further use.
   b) Animal Tissues (Chicken Meat, Chicken Liver, Pork Meat, Pork Liver, Etc.)
   The animal tissues are pre-treated by adding 2.0 g homogenized sample into a 50 ml polystyrene centrifugal tube, adding 10 mL methanol-hydrochloric acid solution, vibrating for 5 min, centrifuging at >3000 g for 5 min at room temperature, collecting 200 μl supernatant, adding 600 μl redissolving solution, mixing uniformly, and taking 50 μl for analysis.
   c) Honey Samples
   The honey samples are pre-treated by adding 2.0 g honey into a 50 ml polystyrene centrifugal tube, adding 5 mL deionized water, vibrating with an eddy vibrator till the honey are completely dissolved, and then vibrating with the eddy vibrator for 5 min, centrifuging at >3000 g for 5 min at ambient temperature, collecting 1 ml supernatant, adding 1 ml redissolving solution, vibrating with the eddy vibrator for 30 s, and taking 50 μl for analysis.

2. Detection Using the Kit

The detection process comprises the steps of: adding 50 μl lincomycin standard solution or sample solution into the microtiter wells of the ELISA plate coated with lincomycin-conjugated antigen, adding 50 μl working solution of lincomycin monoclonal antibody, sealing the plate with a cover film, reacting in a incubator at 25° C. for 30 min, removing the liquid from the wells, adding 250 μl washing solution into each well and removing the liquid after 30 s, repeating the washing step for 5 times, and removing the residual liquid with absorbent paper; adding 100 μl working solution of horseradish peroxidase-labeled goat-anti-mouse anti-antibody, reacting in the thermostatic container at 25° C. for 30 min, removing the liquid in the wells, repeating the washing step, adding developing solution A of carbamide peroxide and developing solution B of tetramethylbenzidine (TMB), moderately vibrating, developing color in the thermostatic container at 25° C. in dark for 15 min, adding the 50 μl stopping solution of 2 mol/L hydrochloric acid into each well, moderately vibrating, and detecting the absorbance (OD value) for each well at 450 nm using Microplate Reader.

3. Analysis of the Detecting Result

The percent absorbance is calculated by dividing the average absorbance (B) of the standard solution at each concentration by the absorbance ($B_0$) of the first standard solution (blank standard) and multiplying by 100%. The standard curve is plotted with the semi-log value of the concentration of the lincomycin standard solution (μg/L) as X axis, and the percent absorbance as Y axis. The percent absorbance of the sample solution is calculated according to the same method. The concentration corresponding to each sample is obtained from the standard curve. The amount of residual linxomycin can be calculated from the standard curve.

Example 4

Detection of the Quality of the Kit

1. Experiments on the Precision of Standards

One batch of ELISA plates is taken from each of the three groups of ELISA plates prepared at three different periods. Ten kits are taken from each of the three batches, and 20 microtiter wells are selected from each plate for detection. The absorbance of the standard solution at 1.8 μg/L is detected for calculating coefficient of variation.

TABLE 2

| | | Repetitive experiments of the standards (CV %) | | | | | | | | |
|---|---|---|---|---|---|---|---|---|---|---|
| | | 1 | 2 | 3 | 4 | 5 | 6 | 7 | 8 | 9 | 10 |
| CV % | Batch 01 | 5.3 | 4.2 | 15.7 | 6.9 | 8.6 | 11.5 | 13.7 | 12.4 | 9.4 | 7.5 |
| | Batch 03 | 7.3 | 12.5 | 8.4 | 7.6 | 9.7 | 11.4 | 10.8 | 5.9 | 7.3 | 10.5 |
| | Batch 06 | 11.7 | 6.7 | 8.3 | 14.1 | 8.2 | 12.6 | 6.4 | 13.6 | 7.8 | 13.5 |

As shown from the above results, the coefficients of variation of 10 standards for each batch are in the range of 4.2%-15.7%.

2. Experiments of Precision and Accuracy of the Samples a) Experiments of Precision of the Samples The muscle, liver and honey added with 20 μg/L lincomycin are detected. Five kits are taken from each of three different batches. The experiment is repeated five times for each concentration. The coefficient of variation is calculated for each concentration, respectively. The results are shown in Tables 3-5.

TABLE 3

Repetitive experiments of muscle samples

| Batch No. | Measured value (μg/L) | | | | | coefficient of variation, CV % |
|---|---|---|---|---|---|---|
|    | 16.5 | 19.8 | 15.3 | 17.2 | 14.9 | 11.6 |
| 01 | 17.3 | 14.6 | 19.5 | 18.7 | 15.1 | 12.7 |
|    | 18.9 | 16.2 | 17.9 | 16.3 | 18.7 | 7.3  |
|    | 17.5 | 15.6 | 16.9 | 18.2 | 14.6 | 8.8  |
| 03 | 18.5 | 16.4 | 19.8 | 15.3 | 16.7 | 10.3 |
|    | 19.7 | 19.5 | 16.4 | 18.3 | 15.8 | 9.9  |
|    | 18.5 | 17.3 | 18.1 | 19.9 | 14.3 | 11.8 |
| 06 | 16.7 | 17.4 | 16.2 | 14.7 | 18.9 | 9.2  |
|    | 19.5 | 14.6 | 15.4 | 18.2 | 19.7 | 13.5 |

TABLE 4

Repetitive experiments of liver samples

| Batch No. | Measured value (μg/L) | | | | | coefficient of variation, CV % |
|---|---|---|---|---|---|---|
|    | 14.2 | 16.7 | 19.8 | 18.5 | 14.6 | 14.5 |
| 01 | 16.7 | 15.8 | 16.4 | 19.7 | 18.7 | 9.5  |
|    | 16.2 | 18.4 | 17.3 | 18.9 | 18.5 | 6.2  |
|    | 19.7 | 19.6 | 14.3 | 14.7 | 15.7 | 15.8 |
| 03 | 17.2 | 16.7 | 19.4 | 18.2 | 15.4 | 8.7  |
|    | 19.0 | 18.4 | 16.8 | 14.2 | 19.5 | 12.2 |
|    | 16.9 | 17.2 | 19.3 | 18.5 | 16.4 | 6.8  |
| 06 | 18.3 | 17.4 | 16.2 | 14.7 | 18.9 | 9.8  |
|    | 17.5 | 16.3 | 18.4 | 14.5 | 17.7 | 9.1  |

TABLE 5

Repetitive experiments of honey samples

| Batch No. | Measured value (μg/L) | | | | | coefficient of variation, CV % |
|---|---|---|---|---|---|---|
|    | 18.9 | 20.2 | 21.8 | 18.4 | 19.2 | 6.8 |
| 01 | 18.3 | 19.5 | 20.7 | 21.5 | 18.6 | 6.9 |
|    | 18.3 | 19.6 | 20.3 | 21.7 | 21.9 | 7.4 |
|    | 20.7 | 21.8 | 21.4 | 17.9 | 18.3 | 9.0 |
| 03 | 21.6 | 18.0 | 17.6 | 21.7 | 21.9 | 10.7 |
|    | 18.6 | 19.1 | 19.6 | 20.5 | 21.4 | 5.6 |
|    | 19.2 | 18.6 | 18.4 | 21.2 | 21.8 | 7.9 |
| 06 | 19.7 | 20.4 | 21.6 | 20.5 | 21.3 | 3.7 |
|    | 18.9 | 19.2 | 18.3 | 20.4 | 21.7 | 6.9 |

As shown from the results, the coefficients of variation of muscle, liver and honey samples are all in the range of 3.7%-15.8%.

b) Experiments on the Accuracy of the Samples

Two lincomycin standard solutions of 20 μg/kg (L) and 40 μg/kg (L) are added into the samples for the recovery experiments, respectively. For each concentration, the experiments are performed in quadruplicate in parallel, and the accuracy is calculated respectively.

TABLE 6

Accuracy of the kit

| Adding concentration | | Sample | | | | |
|---|---|---|---|---|---|---|
|  | | Muscle | | Liver | | Honey | |
| (μg/kg) | | 20 | 40 | 20 | 40 | 20 | 40 |
| Accuracy % | 1 | 86.3 | 79.3 | 97.2 | 86.4 | 92.5 | 98.4 |
|  | 2 | 78.2 | 82.5 | 83.7 | 95.6 | 86.7 | 103.8 |
|  | 3 | 97.4 | 94.5 | 84.1 | 97.1 | 98.6 | 106.1 |
|  | 4 | 88.5 | 98.3 | 75.6 | 81.4 | 107.4 | 94.5 |
| Average % | | 87.6 | 88.7 | 85.2 | 90.1 | 96.3 | 100.7 |

As shown from the results, the recovery rate in muscle samples is in the range of 78.2%-98.3%; the recovery rate in liver samples is in the range of 75.6%-97.2%; and the recovery rate in honey samples is in the range of 86.7%-107.4%.

3. Storage Experiments of the Kit

The condition for storing the kit is 2-8° C. According to the results of the detection for 6 months, the maximum absorbance value (blank standard), 50% inhibitory concentration, and actual detection value of lincomycin added to the kits are all in the normal range. Considering the possibility of abnormal conditions during transport and using processes, the kits are placed at 37° C. for 6 days for accelerated aging experiments, and the results indicate that all of the indexes of the kit meet the requirement. Considering the possibility of freezing conditions occurred, the kits are frozen in a refrigerator at −20° C. for 5 days. The results indicate that all of the indexes of the kit also meet the requirement. According to the results above, the kit can be stored at 2-8° C. for more than 6 months.

4. Detection of the Minimal Detection Limit of the Kit

Negative chicken meat and negative honey samples without lincomycin are detected with the kit of the present invention for 20 times, respectively. The minimal detection limit of the kit is represented by the average of the results plus 3 standard deviations.

TABLE 7

Detecting results of negative chicken samples, μg/kg

| | Sample no. | | | | | | | |
|---|---|---|---|---|---|---|---|---|
| | 1 | 2 | 3 | 4 | 5 | 6 | 7 | 8 |
| Measured value | 2.32 | 0.84 | 0.79 | 1.88 | 2.16 | 0.07 | 2.45 | 2.31 |

| | Sample No. | | | | | | | |
|---|---|---|---|---|---|---|---|---|
| | 9 | 10 | 11 | 12 | 13 | 14 | 15 | 16 |
| Measured value | 1.64 | 1.00 | 1.14 | 1.99 | 2.68 | 1.86 | 2.78 | 1.14 |

| | Sample No. | | | | | |
|---|---|---|---|---|---|---|
| | 17 | 18 | 19 | 20 | Average | standard deviation | minimal detection limit |
| Measured value | 1.25 | 2.54 | 1.90 | 1.50 | 1.71 | 0.71 | 3.85 |

TABLE 8

Detecting results of negative honey samples, μg/kg

| | Sample no. | | | | | | | |
|---|---|---|---|---|---|---|---|---|
| | 1 | 2 | 3 | 4 | 5 | 6 | 7 | 8 |
| Measured value | 0.14 | 0.84 | 0.89 | 0.18 | 0.32 | 0.45 | 0.68 | 0.40 |

| | Sample No. | | | | | | | |
|---|---|---|---|---|---|---|---|---|
| | 9 | 10 | 11 | 12 | 13 | 14 | 15 | 16 |
| Measured value | 0.21 | 1.03 | 0.41 | 0.86 | 1.42 | 0.32 | 0.25 | 0.36 |

| | Sample No. | | | | | |
|---|---|---|---|---|---|---|
| | 17 | 18 | 19 | 20 | Mean | standard deviation | minimal detection limit |
| Measured value | 1.49 | 1.19 | 1.16 | 0.59 | 0.66 | 0.41 | 1.90 |

As shown in Tables 7 and 8, the minimal detection limit of the kit according to the present invention is 3.85 μg/kg for chicken samples and 1.90 μg/kg for honey samples, respectively.

The invention claimed is:

1. An ELISA kit for detecting lincomycin comprising a coating antigen and an enzyme labeled reagent, wherein the coating antigen is selected from the group consisting of a lincomycin hapten-carrier protein conjugate, a lincomycin antibody and a secondary lincomycin anti-antibody;
   when the coating antigen is the lincomycin hapten-carrier protein conjugate, the enzyme labeled reagent is an enzyme-labeled secondary lincomycin anti-antibody and the ELISA kit further comprises the lincomycin antibody;
   when the coating antigen is the lincomycin antibody, the enzyme labeled reagent is an enzyme-labeled lincomycin hapten-carrier protein conjugate; and
   when the coating antigen is the secondary lincomycin anti-antibody, the enzyme labeled reagent is an enzyme-labeled lincomycin hapten-carrier protein conjugate and the ELISA kit further comprises the lincomycin antibody;
   and the lincomycin hapten is obtained through the condensation reaction between lincomycin and succinic anhydride; and
   wherein the lincomycin antibody is the monoclonal antibody secreted by hybridoma cell strain C-1-3 deposited under the accession number CGMCC No. 2398.

2. The ELISA kit according to claim 1, characterized in that the labelling enzyme of the enzyme labeled reagent is horseradish peroxidase or alkaline phosphatase.

3. The ELISA kit according to claim 1, characterized in that the secondary lincomycin anti-antibody is goat-anti-mouse anti-antibody.

4. Hybridoma cell strain C-1-3 deposited under the accession number CGMCC No. 2398.

5. Lincomycin monoclonal antibody secreted by hybridoma cell strain C-1-3 deposited under the accession number CGMCC No. 2398.

* * * * *

UNITED STATES PATENT AND TRADEMARK OFFICE
CERTIFICATE OF CORRECTION

PATENT NO. : 8,507,214 B2  Page 1 of 1
APPLICATION NO. : 12/988111
DATED : August 13, 2013
INVENTOR(S) : He et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this

Fifteenth Day of September, 2015

Michelle K. Lee
*Director of the United States Patent and Trademark Office*